(12) United States Patent
Li et al.

(10) Patent No.: US 8,841,611 B2
(45) Date of Patent: Sep. 23, 2014

(54) MULTI-CAPILLARY COLUMN AND HIGH-CAPACITY IONIZATION INTERFACE FOR GC-MS

(71) Applicant: Agilent Technologies, Inc., Loveland, CO (US)

(72) Inventors: Gangqiang Li, Loveland, CO (US); Maozi Liu, Loveland, CO (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 14/054,703

(22) Filed: Oct. 15, 2013

(65) Prior Publication Data

US 2014/0151546 A1 Jun. 5, 2014

Related U.S. Application Data

(60) Provisional application No. 61/731,629, filed on Nov. 30, 2012.

(51) Int. Cl.
*G01N 30/72* (2006.01)
*G01N 30/02* (2006.01)
*B01D 53/14* (2006.01)

(52) U.S. Cl.
CPC .................................. *G01N 30/7206* (2013.01)
USPC .......... 250/288; 250/281; 250/282; 73/23.35; 73/23.37; 73/23.22; 96/105; 95/15; 95/28

(58) Field of Classification Search
USPC ....... 250/281, 282, 288, 298, 396 R; 73/23.2, 73/23.22, 23.27, 23.35, 23.37, 23.39; 96/101, 105, 106; 95/15, 28
See application file for complete search history.

(56) References Cited

U.S. PATENT DOCUMENTS

| | | | |
|---|---|---|---|
| 4,641,541 A * | 2/1987 | Sharp | 73/864.81 |
| 6,107,628 A * | 8/2000 | Smith et al. | 250/292 |
| 6,583,408 B2 * | 6/2003 | Smith et al. | 250/288 |
| 7,351,964 B2 | 4/2008 | Tolmachev et al. | |
| 7,473,893 B2 * | 1/2009 | Lopez-Avila et al. | 250/288 |
| 7,495,212 B2 | 2/2009 | Kim et al. | |
| 8,124,930 B2 | 2/2012 | Wang | |
| 2002/0175278 A1 | 11/2002 | Whitehouse | |
| 2007/0256474 A1 * | 11/2007 | Paakkanen et al. | 73/23.37 |
| 2008/0087817 A1 * | 4/2008 | Lopez-Avila et al. | 250/288 |
| 2009/0308137 A1 * | 12/2009 | Currie et al. | 73/23.35 |
| 2011/0147575 A1 | 6/2011 | Mordehai et al. | |

FOREIGN PATENT DOCUMENTS

EP 2405463 A1 11/2012

OTHER PUBLICATIONS

Baumbach, Jörg Ingo; Ion mobility spectrometry coupled with multi-capillary columns for metabolic profiling of human breath; Journal of Breath Research; 3(2009) 034001; 16pp.
Varentsov, V.L. et al.; A cooler for intense low-energy ion beams; Nuclear Instruments and Methods in Physics Research; A 490 (2002) 16-29.
Pongpun, et al.; Comparison of a jet separator and an open splitter as an interface between a multi-capillary gas chromatographic column and a time-of-flight mass spectrometer; Journal of Mass Spectrometry; 35, 1105-1111 (2000).

* cited by examiner

Primary Examiner — Bernard E Souw

(57) ABSTRACT

A gas chromatograph-mass spectrometer (GC-MS) system includes a multi-capillary GC column coupled to a mass analyzer through an ionization interface. The ionization interface includes an ionization device and an ion guide configured for receiving a high-capacity gas-sample flow from the GC column and transmitting a compressed ion beam to the mass analyzer. The ion beam may be converging.

20 Claims, 8 Drawing Sheets

MULTI-CAPILLARY COLUMN AND HIGH-CAPACITY IONIZATION INTERFACE FOR GC-MS

RELATED APPLICATIONS

This application claims the benefit of U.S. Provisional Patent Application Ser. No. 61/731,629, filed Nov. 30, 2012, titled "MULTI-CAPILLARY COLUMN AND HIGH-CAPACITY IONIZATION INTERFACE FOR GC-MS," the content of which is incorporated by reference herein in its entirety.

TECHNICAL FIELD

The present invention relates generally to gas chromatography-mass spectrometry (GC-MS), and in particular relates to coupling a multi-capillary GC column with an MS system.

BACKGROUND

A mass spectrometry (MS) system in general includes an ion source for ionizing components of a sample of interest, a mass analyzer for separating the ions based on their differing mass-to-charge ratios (or m/z ratios, or more simply "masses"), an ion detector for counting the separated ions, and electronics for processing output signals from the ion detector as needed to produce a user-interpretable mass spectrum. Typically, the mass spectrum is a series of peaks indicative of the relative abundances of detected ions as a function of their m/z ratios. The mass spectrum may be utilized to determine the molecular structures of components of the sample, thereby enabling the sample to be qualitatively and quantitatively characterized.

In certain "hyphenated" or "hybrid" systems, the sample supplied to the ion source may first be subjected to a form of analytical separation. For example, in a gas chromatography-mass spectrometry (GC-MS) system, the output of the GC column may be transferred into the ion source through appropriate GC-MS interface hardware. In a gas chromatograph, a sample to be analyzed is carried in a gas stream (mobile phase) through the GC column, which includes a stationary phase that causes separation of different components of the sample. The gas-sample mixture is then introduced into the ion source. For GC-MS, the ion source is typically an electron impact (EI) source, chemical ionization (CI) source, or a photo-ionization (PI) source.

The mass analyzer must be operated at a very low pressure (e.g., less than $10^{-5}$ Torr) to avoid ion-molecule reactions. Also, the ion source is typically operated at a very low pressure (e.g., less than $10^{-3}$ Torr) to facilitate interfacing with the mass analyzer and in some cases (e.g., EI) to ensure proper operation. Consequently, to preserve vacuum conditions the gas flow into the mass spectrometer is limited to a small rate, typically 1-10 mL/min. Therefore, in a typical GC-MS system the GC column has a very small bore (i.e., a capillary column), with an inside diameter typically not larger than 0.5 mm. In contrast to the mass spectrometer, the gas chromatograph typically operates at atmospheric pressure (about 760 Torr, or 1 atm) at the column outlet to achieve effective chromatographic separation. This large difference in operating pressures presents a challenge when coupling a gas chromatograph to a mass spectrometer. In some known GC-MS systems, ions produced in the ion source are transferred to the mass analyzer by way of a small-bore aperture. The low molecular weight carrier gas (e.g., helium, nitrogen, argon, or hydrogen) from the GC column is preferentially removed from ion source via a vacuum pump, while the heavier analyte ions are drawn into the sampling aperture. The sampling aperture is small enough to avoid breaking the vacuum inside the mass spectrometer. However, the small size of the sampling aperture results in low ion collection efficiency. That is, most ions produced in the ion source do not enter the sampling capillary, and thus are not mass-analyzed and do not contribute the ion signal utilized to construct the mass spectrum.

The use of a multi-bore capillary column or a multi-channel column (or multi-capillary column, or MCC) as a GC column is of interest. An MCC may consist of a bundle of hundreds of individual capillaries or a single tube with multiple channels, each capillary or channel providing a stationary phase and defining an individual flow path for a gas-sample mixture. The MCC can enable fast-speed, high-resolution analysis while offering high-capacity gas-sample flow without sacrificing column efficiency. The column flow in an MCC may be, for example, two to three orders of magnitude higher than the flow in a typical single-capillary column. Due to the parallel operation of multiple capillaries, the column length can be shortened. The high capacity and short length of the MCC can reduce GC analysis time down to a few minutes. The higher flow rate also enables isothermal separation of volatile organic compounds at ambient temperature.

The MCC, with its high capacity (high flow rate and high total gas flow), may be compatible for coupling with a traditional GC detector employed in a one-dimensional analysis (e.g., when a mass spectrometer is not utilized as the detector), such as a flame ionization detector (FID) or a thermal conductivity detector (TCD). Due to its inherent design (e.g., high capacity and operating pressure), however, the MCC is not readily adaptable for use in conjunction with a mass spectrometer. In a previous investigation, a heated jet separator was positioned outside an evacuated ionization chamber ($10^{-6}$ mbar) of a mass spectrometer. The jet separator was coupled between an MCC (900 capillaries, total gas flow rate on the order of 200 mL/min) in a GC oven and an EI source in the ionization chamber. Inside the jet separator housing, an expansion chamber separated the end of the MCC outlet and the beginning of an aperture leading to the EI source. The expansion chamber was in open communication with a vacuum port leading to a rotary pump to pump carrier gas away from the higher-mass analyte molecules. Such a configuration does not provide an acceptable level of ion collection and transfer efficiency.

Therefore, there is a need for systems, devices and methods for interfacing an MCC with a mass spectrometer. For instance, it would be desirable to provide a solution for interfacing an MCC gas chromatograph with a mass spectrometer in which the operating pressure is transitioned from that of the gas chromatograph down to the vacuum level of the mass spectrometer, while providing high ion collection and transfer efficiency, and while preserving the advantages of the MCC such as fast analysis and high capacity.

SUMMARY

To address the foregoing problems, in whole or in part, and/or other problems that may have been observed by persons skilled in the art, the present disclosure provides methods, processes, systems, apparatus, instruments, and/or devices, as described by way of example in implementations set forth below.

According to one embodiment, a gas chromatograph-mass spectrometer (GC-MS) system includes: a column comprising a column outlet and a plurality of capillaries arranged for establishing respective, simultaneous gas flows to the column outlet; an ionization interface communicating with the column outlet and comprising an ionization device and an ion guide, the ion guide comprising a guide entrance, a guide exit and a plurality of guide electrodes arranged around a guide axis and between the guide entrance and the guide exit, wherein the guide electrodes are configured for constraining ions to an ion beam that radially converges toward the guide exit; and a mass analyzer communicating with the guide exit.

According to another embodiment, a method for acquiring a mass spectrum from a sample gas includes: flowing the sample gas simultaneously through a plurality of capillaries of a gas chromatograph and into an ionization interface; ionizing the sample gas in the ionization interface to produce ions; transmitting the ions through an ion guide and into a mass analyzer; while transmitting the ions, confining the ions to an ion beam that radially converges along an axial length of the ion guide; and while ionizing and transmitting the ions, maintaining the ionization interface at an intermediate pressure between a pressure in the gas chromatograph and a pressure in the mass analyzer.

According to another embodiment, a GC-MS system is configured for performing the method of any of the methods disclosed herein.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

DETAILED DESCRIPTION

Figure 1:
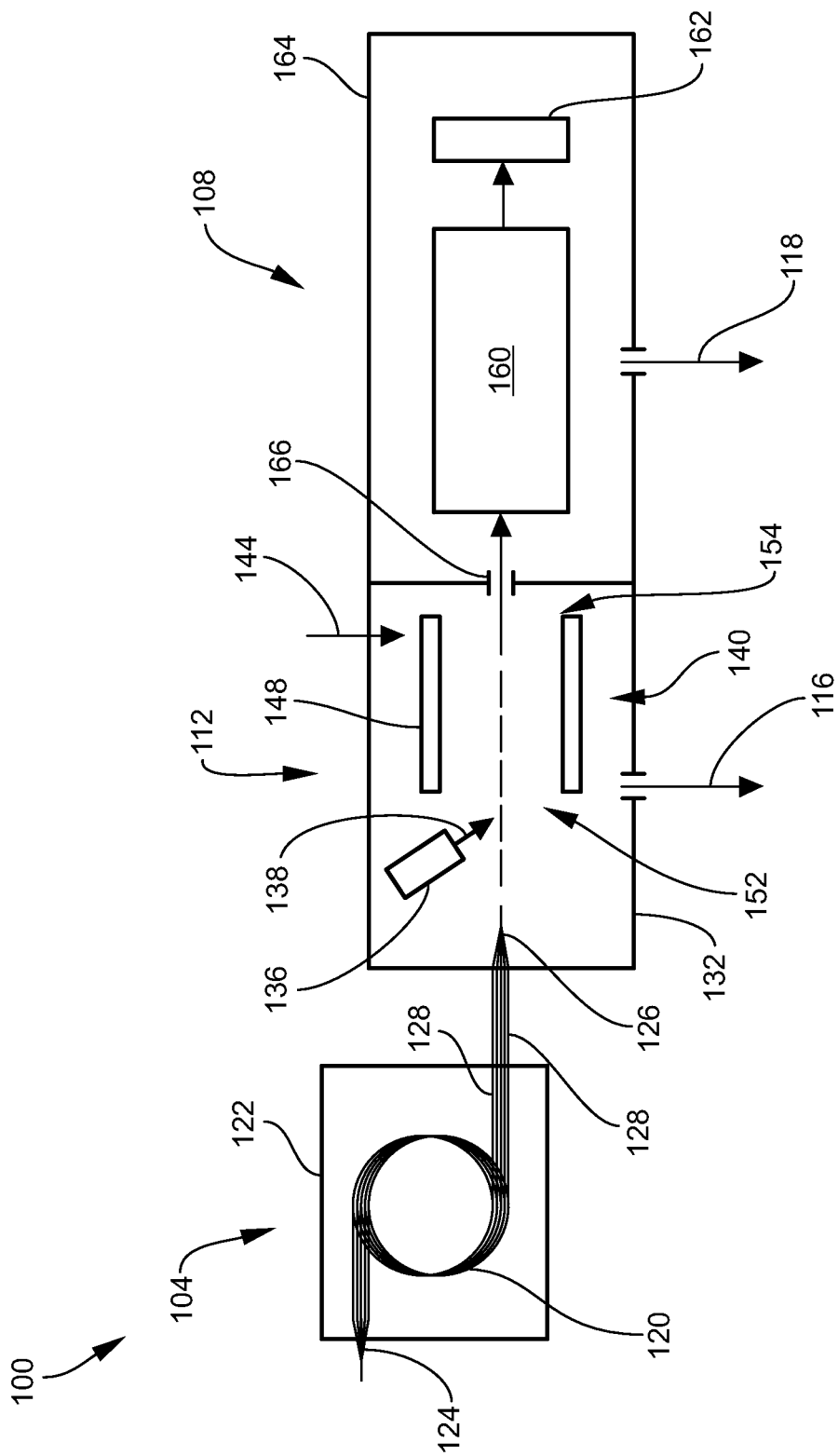
FIG. 1 is a schematic view of an example of a gas chromatograph-mass spectrometry (GC-MS) system according to one embodiment.

FIG. 1 is a schematic view of an example of a gas chromatograph-mass spectrometry (GC-MS) system 100 according to one embodiment. The GC-MS system 100 generally includes a gas chromatograph (GC) 104, a mass spectrometer (MS) 108, an ionization interface 112 coupling the GC 104 to the MS 108, and a vacuum system for maintaining the interiors of the ionization interface 112 and MS 108 at controlled, sub-atmospheric pressure levels. The vacuum system is schematically depicted by vacuum lines 116 and 118 leading from the ionization interface 112 and MS 108, respectively. The vacuum lines 116 and 118 are schematically representative of one or more vacuum-generating pumps and associated plumbing and other components appreciated by persons skilled in the art. The structure and operation of various types of GCs, MSs and associated components are generally understood by persons skilled in the art, and thus will be described only briefly as necessary for understanding the presently disclosed subject matter. In practice, the ionization interface 112 may be integrated with the MS 108 or otherwise considered as the front end or inlet of the MS 108, and thus in some embodiments may be considered as a component of the MS 108.

The GC 104 may generally include a GC column 120 (analytical column) disposed in a housing 122. The GC 104 may also include a heating device (not shown) configured for indirect heating (e.g., a GC oven) or direct heating (e.g., resistive heating element) of the GC column 120, a carrier gas source (not shown), and a sample introduction device (not shown) that establishes a mixed flow of carrier gas and sample vapor into the GC column 120. The sample may be a matrix that includes sample material to be analytically separated in the GC column 120 and one or more solvents, and which is carried by the carrier gas (e.g., helium, nitrogen, argon, hydrogen, etc.) through the GC column 120 and into the ionization interface 112.

In the present embodiment, the GC column 120 is a multi-capillary column (MCC) that includes a column inlet 124, a column outlet 126, and a plurality of individual capillaries or channels 128 communicating with the column inlet 124 and column outlet 126. For convenience, as used herein the terms "multi-bore capillary column," "multi-capillary column" and "MCC" encompass the term "multi-channel column," and the term "capillary" or "capillaries" encompasses the term "channel" or "channels." The capillaries 128 establish individual gas flow paths from the column inlet 124 to the column outlet 126. The capillaries 128 are arranged in parallel in a two-dimensional bundle or array (from the perspective of a plane perpendicular to the drawing sheet). The capillaries 128 are "parallel" in the sense that they all run along the same path, which may include a coiled or looped section as shown in FIG. 1. By this configuration, the capillaries 128 establish simultaneous, individual gas flows (and thus implement simultaneous, individual separation processes) through the GC column 120. In some embodiments, the column inlet 124 is a single inlet and the column outlet 126 is a single outlet, and an outer tube surrounds the capillaries 128. The GC column 120 may include any suitable structures (e.g., plenums) for transitioning from the column inlet 124 to the individual capillary inlets, and from the individual capillary outlets to the column outlet 126. As the capillaries 128 operate as individual analytical separation columns, they may include respective supports for a stationary phase. The capillaries 128 may be open-bore capillaries in which the stationary phase is provided on a film lining the inside walls of each capillary bore, or alternatively may be packed columns in which the stationary phase is provided as a packing in each bore.

In various embodiments, the number of capillaries or channels 128 is in the tens or hundreds or over one thousand. In some embodiments, the length of the capillaries or channels 128 ranges from 40 mm to 10 m. In some embodiments, the inside diameter of the capillaries or channels 128 ranges from 20 μm to 200 μm. In some embodiments, the capillaries 128 collectively provide an effective diameter ranging from 500 μm to 5 mm. In some embodiments, in operation the total volumetric flow rate of the carrier gas-sample mixture through the column 120 (collectively) ranges from 1 to 2000 mL/min. In some embodiments, the total amount of sample-gas material emitted by the column 120 into the ionization interface 112 (during a typical experiment) ranges from 1 fg to 100 μg. Typically, in operation the gas pressure in the GC column 120 (e.g., at the column outlet 126) is around atmospheric pressure or sub-ambient pressure (i.e., around 760 Torr (1 atm) or less than 760 Torr).

In the present embodiment, the column outlet 126 may extend into the ionization interface 112 or communicate with an opening into the ionization interface 112. The column outlet 126 (or an opening) may alternatively be referred to as a sample inlet (or gas-sample inlet) into the ionization interface 112. The capillaries or channels 128 may terminate in the GC column 120 at a point outside the ionization interface 112, or may terminate closer to the column outlet 126 at a point inside the ionization interface 112.

The ionization interface 112 may include an ionization chamber 132 that receives the sample, an ionization device 136 positioned in the chamber to provide energy (schematically depicted as a beam 138) at an ionization region downstream of the column outlet 126, and an ion guide 140 between the column outlet 126 and the low-pressure regions of the MS 108. The vacuum line 116 maintains the chamber 132 at an intermediate pressure between the relatively high pressure of the GC 104 and the relatively low pressure of the MS 108. In some embodiments, the chamber pressure ranges from 0.01 to 100 Torr. The vacuum line 116 also removes non-analytical neutral molecules such as carrier gas and solvents, and in some embodiments removes damping gas (or collision gas) supplied from a damping gas source 144, from the chamber 132. The optional damping gas is an inert gas (e.g., helium, nitrogen, argon, etc.) that reduces the kinetic energy of analyte ions ("thermalizes" or "cools" the ions) in the ion guide 140 by collisions, under conditions (pressure, ion energies) that do not induce ion fragmentation or dissociation. The damping gas may be useful for slowing down neutral analyte molecules to increase the window of time available for their ionization, assisting in producing a compressed ion beam in the ion guide 140, and/or reducing the energy spread of the ions.

The ionization device 136 may be any device suitable for producing analyte ions from the sample stream eluted from the GC column 120, and which is operable and effective at the intermediate pressures contemplated. Examples include, but are not limited to, photo-ionization (PI) devices, chemical ionization (CI) devices, field ionization (FI) devices, and corona discharge devices. Examples of PI devices include resonance-based photon emitters and excimer-based photon emitters. The photoemission may be coherent as in the case of a laser, or non-coherent as in the case of a DC- or AC-powered plasma (or glow discharge) or a dielectric barrier discharge (DBD). The wavelength of the photons may be in the ultraviolet (UV) range (10 nm to 400 nm) or specifically in the vacuum UV (VUV) sub-range (200 nm or lower). A plasma-based PI device may be windowless and allow the energetic species (ions, electrons, metastables, etc.) of the plasma to interact with the sample, or may include a window that isolates the plasma and transmits only the photons generated by the plasma to the sample. The structure of the ionization device 136 may be located outside the ion guide 140 and positioned to direct the energy beam 138 toward an ionization region primarily located between the column outlet 126 and ion guide 140 (as illustrated in FIG. 1), or may be located outside the ion guide 140 and oriented to direct the energy beam 138 into the ion guide 140, or may be located at the ion guide's entrance or inside the ion guide 140. In some embodiments, the ionization device 136 is representative or two or more ionization devices, which may be of the same type or different type.

The ion guide 140 may include a set of ion guide electrodes 148 arranged about an ion guide axis and surrounding an interior of the ion guide 140, an ion guide entrance 152 leading into the interior, and an ion guide exit 154 leading out from the interior. The ion guide electrodes 148 may be in signal communication with one or more radio frequency (RF) voltage sources and direct current (DC) sources (not shown). An RF voltage or composite RF/DC voltage is applied to at least some of the ion guide electrodes 148 at an RF voltage drive frequency and magnitude suitable for generating a periodic, two-dimensional RF confining field that repels ions of a desired m/z range (i.e., analyte ions) away from the ion guide electrodes 148, in a manner analogous to the RF trapping field applied by a linear ion trap. Hence, the RF confining field constrains the radial component of ion motion whereby the ions are focused in an ion cloud or beam along the ion guide axis. The damping gas (when employed) may assist in focusing the ions. In some embodiments, examples of which are described below, the ion guide electrodes 148 are configured to compress the ion beam such that the cross-sectional area of the ion beam (in the x-y plane perpendicular to the drawing sheet) converges in the direction of the ion guide exit 154. By such configuration, the ion beam acceptance is defined by the ion guide entrance 152 and a final ion beam emittance smaller than the beam acceptance is defined by the ion guide exit 154 (or by a conductance-limiting aperture adjacent to the ion guide exit 154). The selection of the RF voltage drive frequency and magnitude will depend on factors such as the m/z range to be stably focused and transmitted. In some embodiments, the RF voltage drive frequency ranges from 10 kHz to 10 MHz and the voltage magnitude ranges from 10 V to 1000 V peak-to-peak.

Separately, in some embodiments a DC voltage is applied to one or more of the ion guide electrodes 148, and/or to additional ion optics components near the ion guide entrance 152 and ion guide exit 154, so as to generate an axial DC voltage gradient (and resulting accelerating field) sufficient to promote motion of the ions toward the ion guide exit 154. The DC voltage may be useful for preventing ion stalling that may result from the use of damping gas, and/or preventing ion stalling or reflection (back toward the ion guide entrance 152) that may result from the RF confining field at a small ion guide exit 154. In some embodiments, the ion guide 140 transmits ions to the MS 108 efficiently without the use of either a flow of damping gas or an axial DC field.

Generally, the ion guide 140 may have a configuration effective for receiving a high gas flow from the MCC GC column 120 and collecting a large amount of analyte ions from the ionization region with high (up to 100%) efficiency. The ion guide entrance 152 may be relatively large, in some embodiments ranging from 0.3 cm to 3 cm in diameter. The ion guide 140 may have a configuration effective for compressing the ions to a narrow beam and transferring the ions into the MS 108 with high (up to 100%) efficiency, i.e., with minimal ion loss and minimal inclusion of non-analyte species. The ion beam may have a converging profile. In some embodiments, the converging ion beam is realized by the ion guide electrodes 148 likewise having a converging profile such that the cross-sectional area of the ion guide exit 154 is less than the cross-sectional area of the ion guide entrance 152. Examples of the foregoing include electrode configurations termed "ion funnels." In some embodiments, the guide exit 154 has an inside diameter ranging from 50 to 97% smaller than an inside diameter of the guide entrance 152. In other embodiments, the converging ion beam is realized by the ion guide electrodes 148 generating an RF confining field whose characteristics vary in the axial direction. The ion guide electrodes 148 may be arranged in an "open" configuration that provides multiple pathways for neutral gas/vapor species from the GC column 120 to flow toward the vacuum line 116, and for damping gas to flow through the ion guide 140 and toward the vacuum line 116. The ion guide 140 may thus serve as a filter for material that does not contribute to the MS signal. Examples of the ion guide 140 are described further below.

The MS 108 may generally include a mass analyzer 160 and an ion detector 162 enclosed in a housing 164. The vacuum line 118 maintains the interior of the mass analyzer 160 at very low (vacuum) pressure. In some embodiments, the mass analyzer pressure ranges from $10^{-4}$ to $10^{-9}$ Torr. The vacuum line 118 also removes any residual non-analytical neutral molecules from the MS 108. FIG. 1 schematically illustrates an ion sampling line 166 between the ionization interface 112 and the mass analyzer 160. The ion sampling line 166 may be any component or combination of components configured for enabling the analyte ions to be transferred from the ion guide exit 154 into the mass analyzer 160 with minimal or no loss of ions, with minimal non-analytical components such as neutral species, and without breaking the vacuum of the MS 108. The ion sampling line 166 may, for example, include one or more of the following, as appreciated by persons skilled in the art: capillary, orifice, ion optics, skimmer plate, ion guide, ion slicer, aperture, etc.

The mass analyzer 160 may be any device configured for separating, sorting or filtering analyte ions on the basis of their respective m/z ratios. Examples of mass analyzers include, but are not limited to, multipole electrode structures (e.g., quadrupole mass filters, ion traps, etc.), time-of-flight (TOF) analyzers, ion cyclotron resonance (ICR) traps, and ion mobility spectrometers (IMS). The mass analyzer 160 may include a system of more than one mass analyzer, particularly when ion fragmentation is desired. As examples, the mass analyzer 160 may be a tandem MS or MS$^n$ system, as appreciated by persons skilled in the art. As another example, the mass analyzer 160 may include a mass filter followed by a collision cell, which in turn is followed by a mass filter (e.g., a triple-quad, or QQQ, system) or TOF device (e.g., a qTOF system).

The ion detector 162 may be any device configured for collecting and measuring the flux (or current) of mass-discriminated ions outputted from the mass analyzer 160. Examples of ion detectors include, but are not limited to, electron multipliers, photomultipliers, and Faraday cups.

Figure 2:
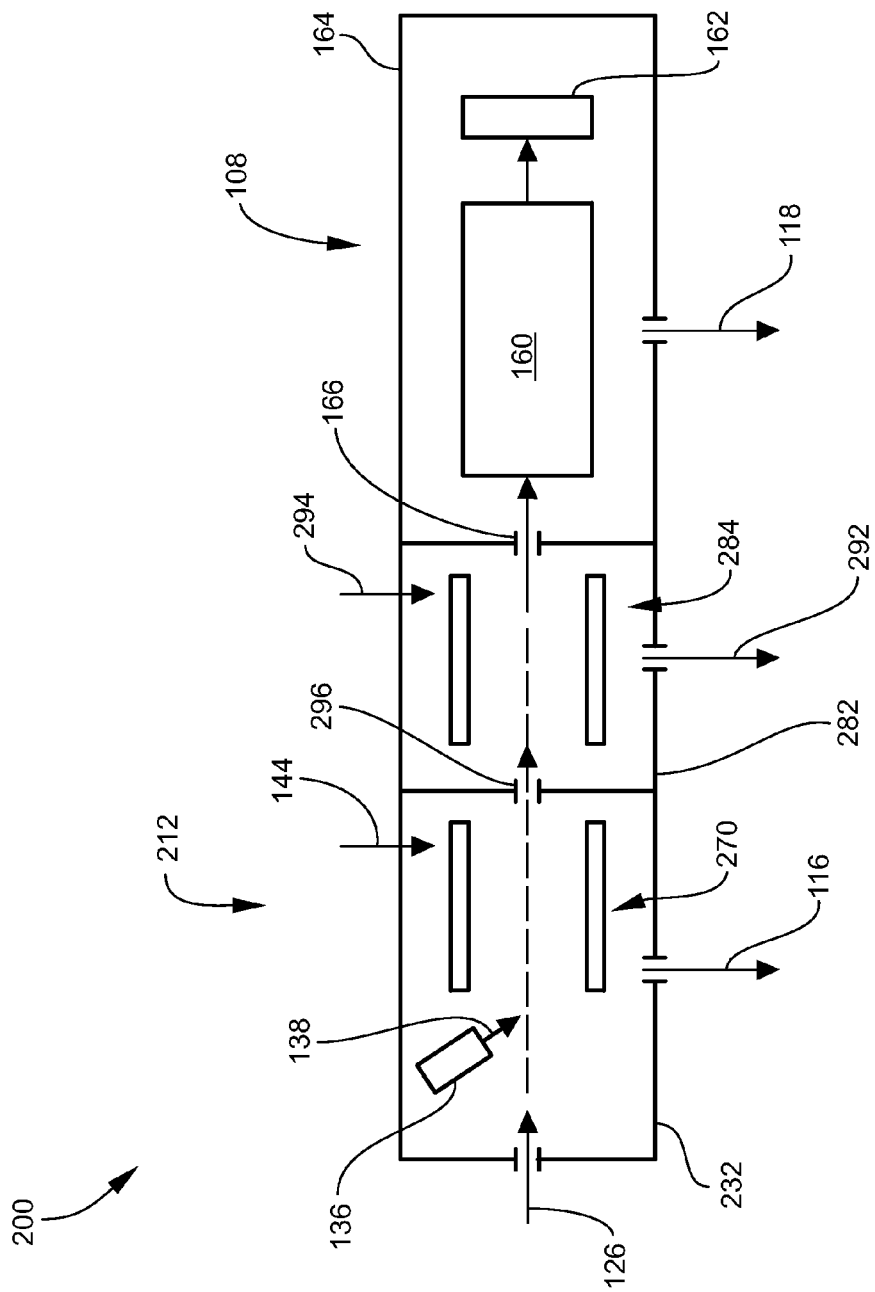
FIG. 2 is a schematic view of an example of a GC-MS system according to another embodiment.

FIG. 2 is a schematic view of an example of a GC-MS system 200 according to another embodiment. Various components of the GC-MS system 200 may be the same as or similar to components described above and illustrated in FIG. 1, and are designated by similar reference numerals. In the present embodiment, the GC-MS system 200 includes an ionization interface 212 that includes multiple separate differential pumping stages and thus multiple discrete intermediate pressure regions. Two pumping stages are illustrated in FIG. 2 by example only. In the illustrated example, the ionization interface 212 includes a first chamber 232 that may correspond to the ionization chamber described above and illustrated in FIG. 1. Hence, the first chamber 232 communicates with the GC column outlet 126, the vacuum line 116, and optionally a damping gas source 144. The first chamber 232 includes the ion source(s) 136 and a first ion guide 270. The ionization interface 212 also includes a second chamber 282 between the first chamber 232 and the mass analyzer 160. The second chamber 282 includes a second ion guide 284, a dedicated vacuum line 292, and optionally a damping gas source 294. The second chamber 282 communicates with the mass analyzer 160 via the ion sampling line 166.

The second chamber 282 is fluidly isolated from the first chamber 232 by a suitable boundary or partition. However, the second chamber 282 communicates with the first chamber 232 via an ion transfer line 296 formed in or passing through the partition. The ion transfer line 296 may be any component or combination of components configured for enabling the analyte ions to be transferred from the first ion guide 270 into the second ion guide 284 with minimal or no loss of ions, and while maintaining the respective pressure levels in the first chamber 232 and second chamber 282. The ion transfer line 296 may, for example, be or include an appropriately sized orifice. The ion transfer line 296 may alternatively or additionally include an aperture, ion optics, etc. The vacuum system (via vacuum lines 116 and 292) maintains the first chamber 232 and second chamber 282 at respective intermediate pressures between the relatively high pressure of the GC 104 (FIG. 1) and the relatively low pressure of the MS 108, with the pressure in the second chamber 282 being lower than the pressure in the first chamber 232. In some embodiments, the pressure in the first chamber 232 (first intermediate pressure) ranges from 100 to 5 Torr, and the pressure in the second chamber 282 (second intermediate pressure) ranges from 5 to 0.01 Torr.

The second chamber 282 may implement one or more of the following functions: providing an additional step-down in pressure between the GC 104 and MS 108; providing an additional step-down in gas flow between the GC 104 and MS 108; removing additional non-analytical neutral molecules from the ion path; and providing additional processing of the ion beam, such as focusing, cooling and reducing of energy spread. The first ion guide 270 may be configured and operated as described above in conjunction with FIG. 1. The second ion guide 284 may have the same configuration as the first ion guide 270 or may be different. For example, the first ion guide 270 may have an ion funnel-type configuration while the second ion guide 284 is a more conventional multipole ion guide. As another example, the first ion guide 270 and second ion guide 284 may both have ion funnel-type configurations. The axes of the first ion guide 270 and second ion guide 284 may be generally collinear as illustrated, or may be offset by an angle or radial distance such as described in U.S. Patent App. Pub. No. 2011/0147575, the entire content of which is incorporated by reference herein.

In some embodiments, the ionization interface may include more than two chambers as noted above, with each chamber providing an additional step-down in pressure. In some embodiments, the ionization interface of either FIG. 1 or FIG. 2 may include more than one ion guide in series in a single chamber.

Figure 3:
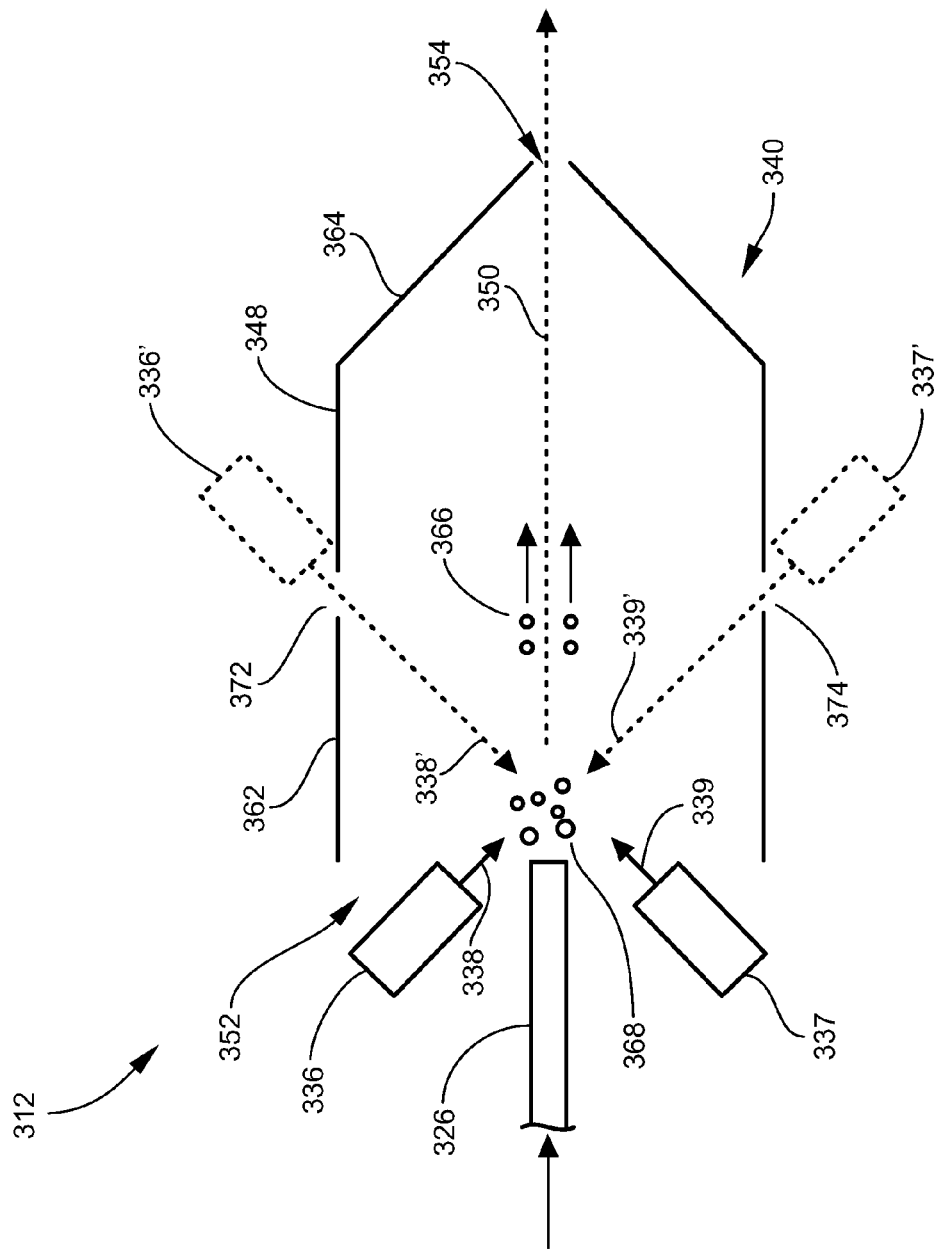
FIG. 3 is a schematic cross-sectional view of an example of an ionization interface according to an embodiment, which may be provided in a GC-MS system.

FIG. 3 is a schematic cross-sectional view of an example of an ionization interface 312 according to another embodiment, which may be provided in a GC-MS system such as illustrated in FIG. 1 or FIG. 2. FIG. 3 illustrates a column outlet 326 from an MCC GC column, a first ionization device 336 emitting energy (depicted by example as a beam 338), a second ionization device 337 emitting energy (depicted by example as a beam 339), and an ion guide 340.

The ion guide 340 includes a plurality of ion guide electrodes 348 arranged about an ion guide axis 350, an ion guide entrance 352, and an ion guide exit 354 axially spaced from the ion guide entrance 352. In operation, radial RF confining fields and axial DC acceleration fields may be generated as described elsewhere in this disclosure. In the present embodiment, the ion guide 340 includes a first section 362 of ion guide electrodes beginning at the ion guide entrance 352, followed by a second section 364 of ion guide electrodes terminating at the ion guide exit 354. The first section 362 has a constant or substantially constant cross-sectional area, and in some embodiments may be a cylindrical section. The first section 362 may be useful for increasing the residence time of neutral analytes in the ion guide 340 to improve ionization yield, for enhancing removal of neutral gas/vapor species, and/or for enhancing thermalization of as-produced analyte ions 366 through increased collisions with a damping gas. The second section 364 has a cross-sectional area that tapers (is reduced) in the direction toward the ion guide exit 354, and in some embodiments may be a conical section. The second section 364 is thus configured for producing a converged ion beam as described elsewhere in this disclosure. The axial lengths of the first section 362 and second section 364 may be the same or substantially the same, or may be different.

In some embodiments, the ion guide 340 may include more than one section of ion guide electrodes of constant cross-sectional area, and/or more than one section of ion guide electrodes of tapering cross-sectional area. A section of constant cross-sectional area may be interposed between two sections of tapering cross-sectional area, and/or a section of tapering cross-sectional area may be interposed between two sections of constant cross-sectional area.

It will be understood that FIG. 3 schematically illustrates the outer profile or envelope of the interior region defined by the electrode set. In practice a number of ion guide electrodes 348, individually addressable by voltage sources, may be spaced from each other circumferentially about the ion guide axis 350, or axially along the ion guide axis 350 such as in the example described below and illustrated in FIG. 4.

In the present embodiment, the column outlet 326 is positioned just upstream, at, or inside the ion guide entrance 352, such that neutral sample components 368 are discharged from the column outlet 326 directly into the ion guide 340 and the ionization region is located at least partially in the ion guide 340. In the present embodiment, the ionization devices 336 and 337 are positioned at or near the ion guide entrance 352, but in other embodiments may be positioned in other locations. As an example, FIG. 3 illustrates an alternative first ionization device 336' and second ionization device 337' positioned outside the ion guide 340 at intermediate points along the axial length of the ion guide 340. Respective energy beams 338' and 339' from the alternative ionization devices 336' and 337' may be transmitted through apertures 372 and 374 formed through certain ion guide electrodes 348 or through spaces between adjacent ion guide electrodes 348. It will be understood that in other embodiments, a single ionization device or more than two ionization devices may be provided, and further that two or more ionization devices of different types may be provided.

Figure 4:
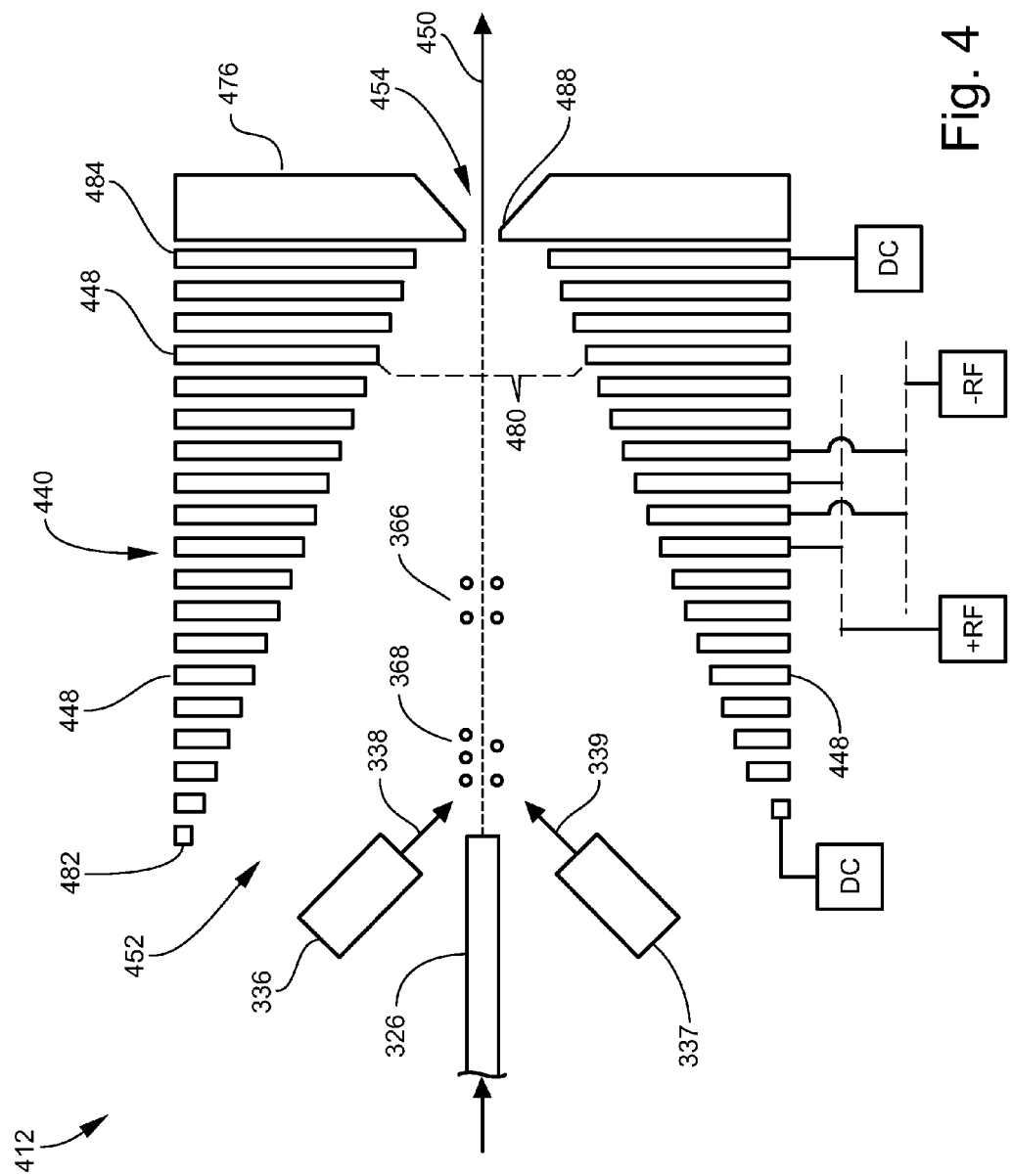
FIG. 4 is a schematic cross-sectional view of an example of an ionization interface according to another embodiment.

FIG. 4 is a schematic cross-sectional view of an example of an ionization interface 412 according to another embodiment, and specifically an example of an ion guide 440 that may be provided in the ionization interface 412. The ion guide 440 includes a plurality of ion guide electrodes 448 arranged about an ion guide axis 450 and surrounding an interior region. One axial end of the ion guide electrodes 448 corresponds to an ion guide entrance 452 and the other axial end corresponds to an ion guide exit 454. The ion guide 440 may also include one or more axially positioned entrance lenses (not shown) and exit lenses 476 as noted above. In this embodiment, the ion guide electrodes 448 include a series of plate-shaped electrodes arranged transversely to the ion guide axis 450 and axially spaced from each other. Each ion guide electrode 448 has an aperture 480 that is typically centered on the ion guide axis 450. The aperture of a first ion guide electrode 482 at the ion guide entrance 452 has the largest cross-sectional area, the aperture of a last ion guide electrode 484 at the ion guide exit 454 has the smallest cross-sectional area, and the apertures of the intermediate ion guide electrodes 448 have one or more intermediate cross-sectional areas. The electrode apertures 480 reduce in cross-sectional area (e.g., reduce in diameter in the case of circular apertures)—and thus the cross-sectional area of the interior region tapers—in the direction of the ion guide exit 454, resulting in an ion funnel configuration. The apertures 480 may be circular or elliptical, or alternatively may be polygonal (e.g., rectilinear), as desired for best accommodating the output geometry of the column outlet 326 and/or the input geometry of the mass analyzer.

In typical implementations, the RF confining field is produced by applying RF voltages to each ion guide electrode 448 such that the RF voltage on any given ion guide electrode 448 is 180 degrees out of the phase with the RF voltage on the adjacent ion guide electrode(s) 448, as schematically shown. DC voltages may be applied to the first ion guide electrode 482, last ion guide electrode 484, and/or one or more of the intermediate ion guide electrodes 448 as needed to control the axial motion of the ions, as schematically shown. This electrode geometry generates a converging ion confining region as described elsewhere in the present disclosure. Some embodiments include the illustrated exit lens 476 (or end plate), which may have an aperture 488 appreciably smaller than that of the last ion guide electrode 484. RF and/or DC voltages may be applied to the exit lens 476, or the exit lens 476 may primarily serve as a conductance limit on the gas flow. In some embodiments, the ion guide 440 may include a section of constant cross-sectional area (such as a section of successive ion guide electrodes 448 with apertures 488 of the same inside diameter) as described above and illustrated in FIG. 3.

Figure 5:
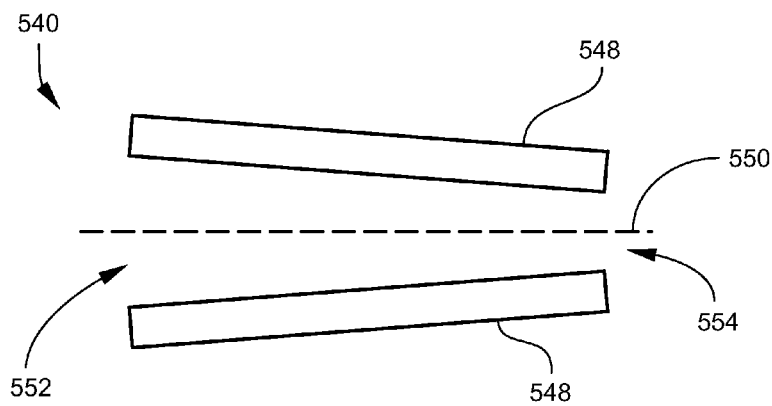
FIG. 5 is a schematic side view of an example of an ion guide according to another embodiment.
Figure 6:
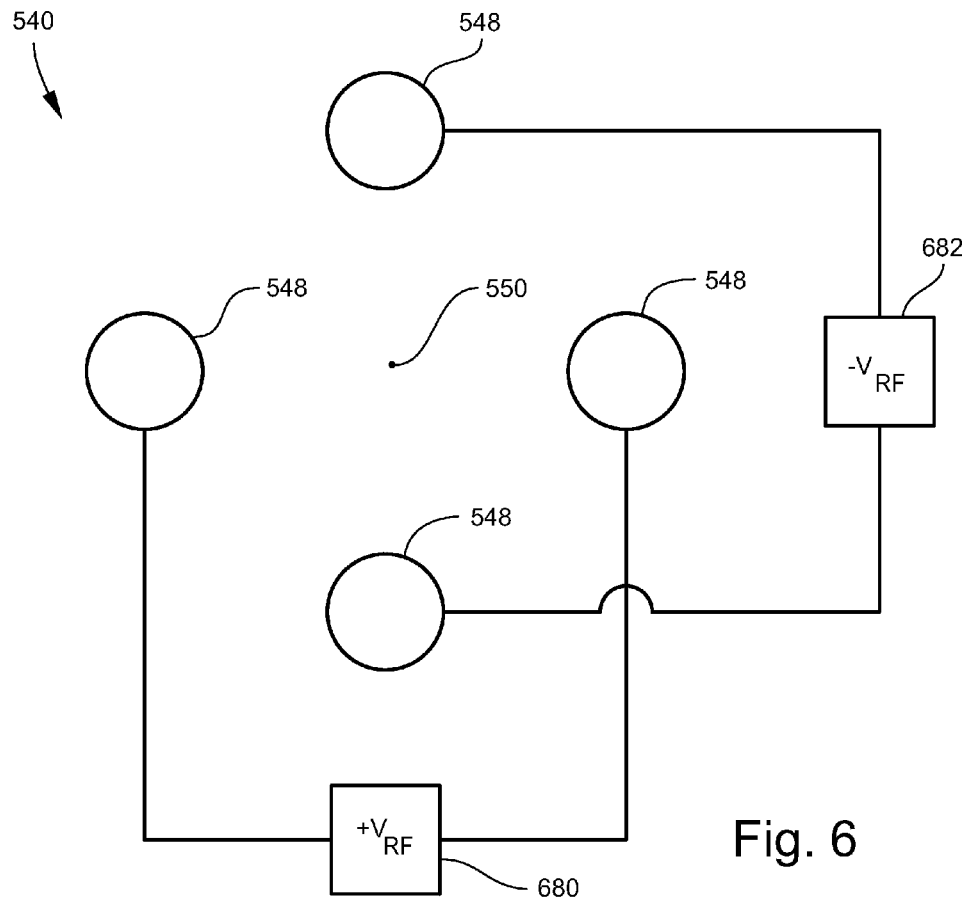
FIG. 6 is a schematic end view of the ion guide illustrated in FIG. 5.

FIG. 5 is a schematic side view of an example of an ion guide 540 according to another embodiment. FIG. 6 is a schematic end view of the ion guide 540. The ion guide 540 includes a plurality of ion guide electrodes 548. The ion guide electrodes 548 are arranged about an ion guide axis 550 and surround an interior region. One axial end of the ion guide electrodes 548 corresponds to an ion guide entrance 552 and the other axial end corresponds to an ion guide exit 554. The ion guide 540 may also include one or more axially positioned entrance and exit lenses (not shown) as noted above. In this embodiment, the ion guide electrodes 548 have a multipole configuration in which each ion guide electrode 548 is elongated generally in a direction from the ion guide entrance 552 to the ion guide exit 554. For clarity, only one opposing pair of ion guide electrodes 548 is shown in FIG. 3. By way of example, FIG. 6 illustrates a quadrupole arrangement in which two opposing pairs of ion guide electrodes 548 are provided. It will be understood, however, that more than two opposing pairs of ion guide electrodes 548 may be provided to realize a higher-order multipole arrangement. In typical implementations, the RF confining field is produced by applying RF voltages to each ion guide electrode 548 such that the RF voltage on any given ion guide electrode 548 is 180 degrees out of the phase with the RF voltage on the adjacent ion guide electrode(s) 548, as schematically depicted by RF voltage sources 680 and 682. DC voltages may be applied to some or all of the ion guide electrodes 548 and/or to entrance and exit lenses as needed to control the axial motion of the ions. Also in this embodiment, the ion guide electrodes 548 are oriented so as to converge toward each other in the direction of the ion guide exit 554, i.e., at an angle to the ion guide axis 550, such that the cross-sectional area of the interior region at the ion guide entrance 552 is greater than the cross-sectional area at the ion guide exit 554. In some embodiments, the ion guide electrodes 548 may be oriented at an angle ranging from about 0.5 degrees to about 10 degrees relative to the ion guide axis 550. This electrode geometry generates a converging ion confining region as described elsewhere in the present disclosure.

Figure 7:
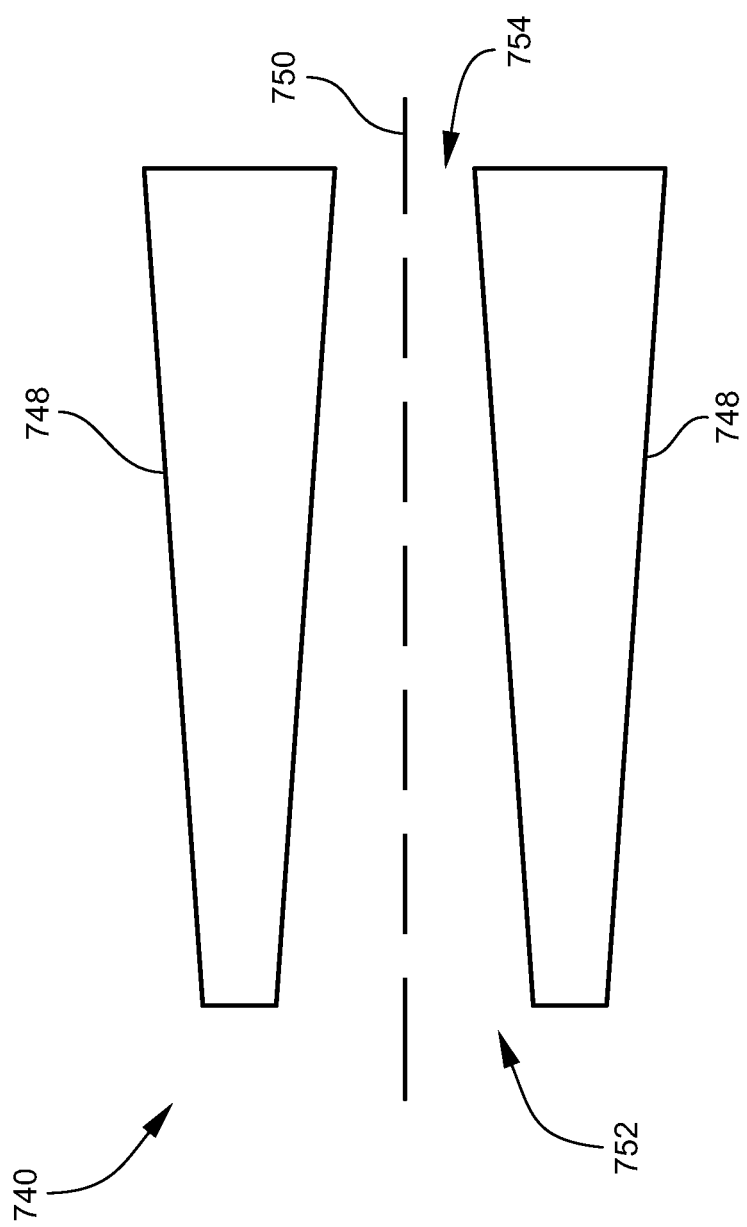
FIG. 7 is a schematic side view of an example of an ion guide according to another embodiment.

FIG. 7 is a schematic side view of an example of an ion guide 740 according to another embodiment. The ion guide 740 includes a plurality of ion guide electrodes 748. The ion guide electrodes 748 are arranged about an ion guide axis 750 and surround an interior region. One axial end of the ion guide electrodes 748 corresponds to an ion guide entrance 752 and the other axial end corresponds to an ion guide exit 754. The ion guide 740 may also include one or more axially positioned entrance and exit lenses (not shown) as noted above. The ion guide electrodes 748 may generally have a multipole configuration as described above in conjunction with FIGS. 5 and 6. In this embodiment, however, the ion guide electrodes 748 may be generally parallel and their diameters are varied along the axial direction such that the cross-sectional area of the interior region at the ion guide entrance 752 is greater than the cross-sectional area at the ion guide exit 754, thereby providing a converging ion confining region as described above. In another embodiment, the ion guide electrodes 748 may be physically converging as shown in FIG. 5 as well as having varying diameters.

Figure 8:
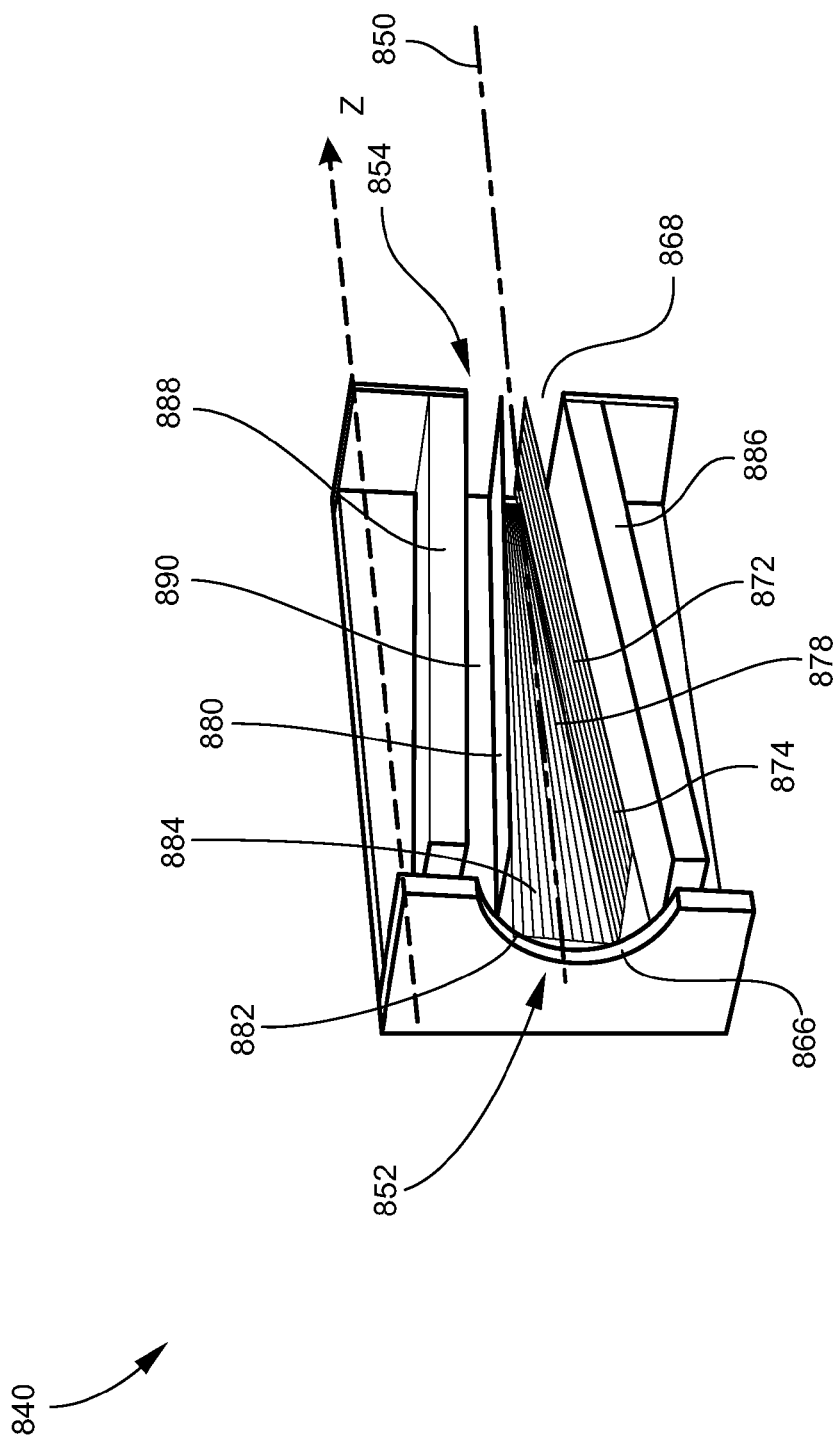
FIG. 8 is a cut-away perspective view of an example of an ion guide according to another embodiment.

FIG. 8 is a cut-away perspective view of an example of an ion guide 840 according to another embodiment. The ion guide 840 may be characterized as providing a longitudinal "RF carpet" arrangement with converging geometry. The ion guide 840 includes a plurality of ion guide electrodes. The ion guide electrodes are arranged about an ion guide axis 850 and surround an interior region. One axial end of the ion guide electrodes corresponds to an ion guide entrance 852 and the other axial end corresponds to an ion guide exit 854. The ion guide 840 may also include one or more axially positioned entrance lenses 866 and exit lenses 868 as noted above. In this embodiment, the ion guide electrodes are elongated generally in a direction from the ion guide entrance 852 to the ion guide exit 854 and have a relatively small cross-sectional dimension (e.g., width in the case of a rectilinear cross-section, or diameter in the case of a circular cross-section). Additionally, the ion guide electrodes are disposed on (or formed on, or supported by) two or more substrates. Thus, in the illustrated example, the ion guide 840 includes a first substrate 872 on which a plurality of first ion guide electrodes 874 are disposed, and an opposing second substrate 880 on which a plurality of second ion guide electrodes (not shown) are disposed. The ion guide 840 may also include a third substrate 882 on which a plurality of third ion guide electrodes 884 are disposed, and an opposing fourth substrate (not shown) on which a plurality of fourth electrodes (not shown) are disposed. Alternatively, contiguous conductive layers may be substituted for one of the opposing sets of ion guide electrodes. The third substrate 882 and fourth substrate may be oriented in planes orthogonal to those of the first substrate 872 and second substrate 880. The first substrate 872 and second substrate 880 may be disposed on respective bases or walls 886 and 888, which in FIG. 8 are shown to be detached for illustrative purposes. The third substrate 882 may similarly be disposed on a base or wall 890, as well as the fourth substrate (not shown).

On any given substrate (e.g., 872, 880, 882), each ion guide electrode is parallel to the other ion guide electrodes. In typical implementations, the RF confining field is produced by applying RF voltages to each ion guide electrode such that the RF voltage on any given ion guide electrode is 180 degrees out of the phase with the RF voltage on the adjacent ion guide electrode(s) on the same substrate. In some embodiments, the RF voltage may be applied to only one pair of opposing electrode sets, such as only to the first ion guide electrodes 874 and second ion guide electrodes, or only to the third ion guide electrodes 884 and fourth ion guide electrodes. DC voltages may be applied to some or all of the ion guide electrodes and/or to entrance lenses 866 and exit lenses 868 as needed to control the axial motion of the ions. In some embodiments, DC voltages may be applied to only one pair of opposing electrode sets or to one pair of opposing contiguous conductive layers. In the illustrated embodiment, the first substrate 872 and the second substrate 880 (and thus the first ion guide electrodes 874 and second ion guide electrodes) are oriented so as to converge in the direction of the ion guide exit 854, i.e., at an angle to the ion guide axis 850, such that the cross-sectional area of the interior region at the ion guide entrance 852 is greater than the cross-sectional area at the ion guide exit 854. In some embodiments, the ion guide electrodes may be oriented at an angle ranging from about 0.5 degrees to about 10 degrees relative to the ion guide axis 850. The third substrate 882 and the fourth substrate (and thus the third ion guide electrodes 884 and fourth ion guide electrodes) may likewise converge toward each other relative to the ion guide axis 850, or alternatively may be parallel to each other. In either case, the electrode geometry illustrated in FIG. 8 generates a converging ion confining region 878 as described above.

As one non-limiting example, the substrates of the ion guide 840 are composed of a suitable dielectric material and the ion guide electrodes are formed on the substrates by any suitable fabrication or microfabrication technique. Each ion guide electrode may have a cross-sectional dimension (e.g., width or diameter) ranging from about 5 µm to about 500 µm, a thickness (or height above the substrate) ranging from about 0.1 µm to about 50 µm, and a pitch (i.e., spacing between adjacent electrodes) ranging from about 10 µm to about 1000 µm.

More generally, the ion guide electrodes have relatively small dimensions as compared, for example, to conventional multipole arrangements of rod-type electrodes. As a result, the RF confining field is maintained in comparative close proximity to the ion guide electrodes and their respective substrates. This in turn results in the field-free or near field-free region through which the ion guide axis 850 passes being larger in comparison to that established by conventional electrode geometries. The resulting spatial form of the electric field may facilitate the generation of a converging ion confining region 878 that has a large ion acceptance aperture and a small ion emittance aperture. Moreover, this configuration may prevent the establishment of a reflective RF field at the ion guide exit 854 that might undesirably reflect ions back toward the ion guide entrance 852.

Figure 9:
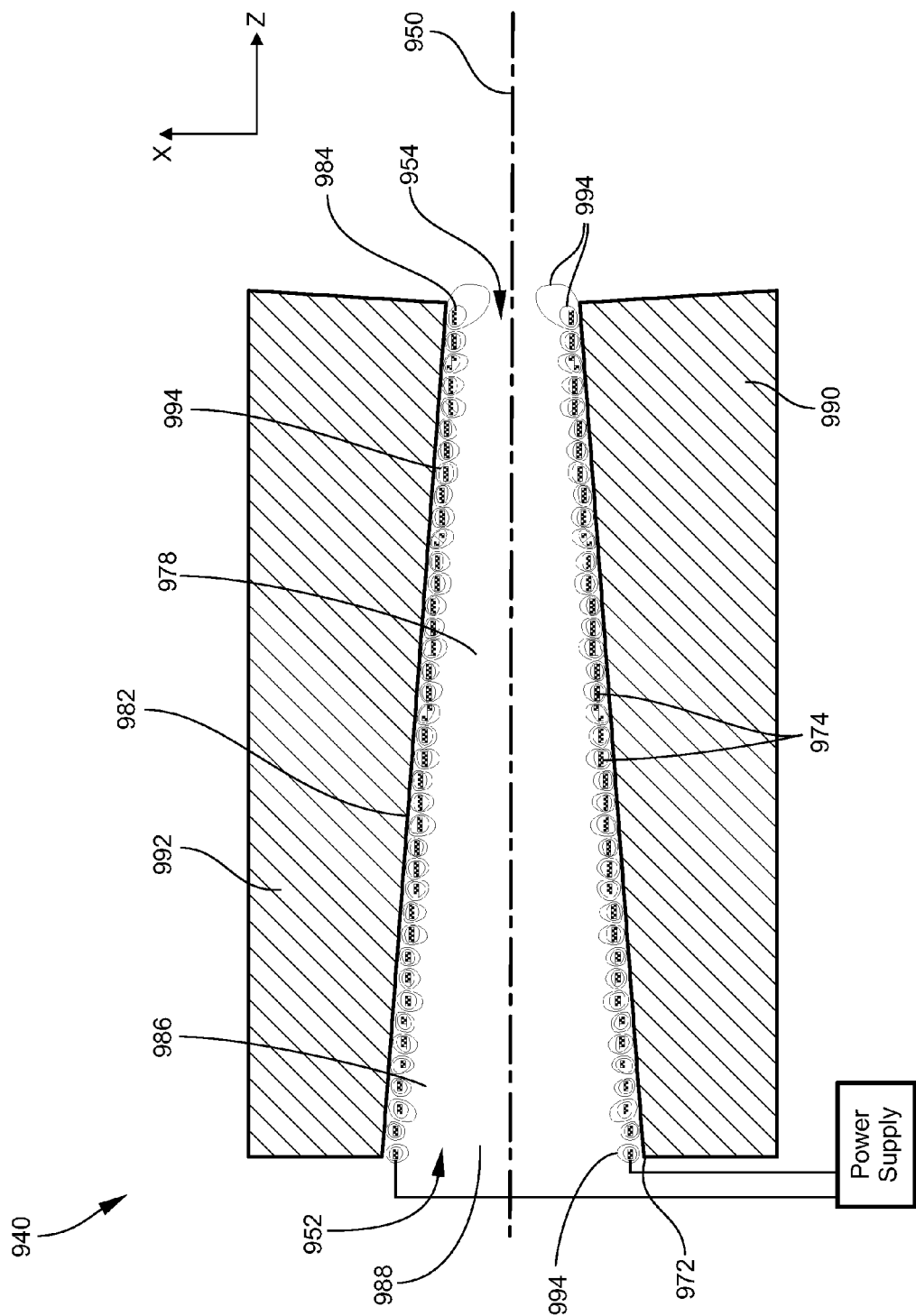
FIG. 9 is a cross-sectional side view of an example of an ion guide according to another embodiment.

FIG. 9 is a cross-sectional side view of an example of an ion guide 940 according to another embodiment. The ion guide 940 may be characterized as providing a transverse "RF carpet" arrangement with converging geometry. The ion guide 940 includes a plurality of ion guide electrodes enclosed in a collision gas chamber (not shown). The ion guide electrodes are arranged about an ion guide axis 950 and surround an interior region. One axial end of the ion guide electrodes corresponds to an ion guide entrance 952 and the other axial end corresponds to an ion guide exit 954. The ion guide 940 may also include one or more axially positioned entrance and exit lenses (not shown) as noted above. The ion guide electrodes have a relatively small cross-sectional dimension as in the case of the electrodes described above in conjunction with FIG. 8. In this embodiment, however, the ion guide electrodes are oriented in a direction orthogonal to those illustrated in FIG. 8, i.e., orthogonal to the X-Z plane depicted in FIG. 9. In the illustrated example, the ion guide 940 includes a first substrate 972 on which a plurality of first ion guide electrodes 974 are disposed, and an opposing second substrate 982 on which a plurality of second ion guide electrodes 984 are disposed. The ion guide 940 may also include a third substrate 986 on which a contiguous conductive layer 988 is disposed, and an opposing fourth substrate (not shown) on which a contiguous conductive layer (not shown) is disposed. Alternatively, a plurality of third ion guide electrodes (not shown) and a plurality of fourth electrodes (not shown) may be disposed on the third substrate 986 and fourth substrate, respectively. The third substrate 986 and fourth substrate may be oriented in planes orthogonal to those of the first substrate 972 and second substrate 982. The first substrate 972 and second substrate 982 may be disposed on respective bases or walls 990 and 992, as well as the third substrate 986 and fourth substrate (not shown).

On any given substrate (e.g., 972, 982, 986), each ion guide electrode is parallel to the other ion guide electrodes. In typical implementations, the RF confining field is produced by applying RF voltages to each ion guide electrode such that the RF voltage on any given ion guide electrode is 180 degrees out of the phase with the RF voltage on the adjacent ion guide electrode(s) on the same substrate. In some embodiments, the RF voltage may be applied to only one pair of opposing electrode sets, such as only to the first ion guide electrodes 974 and second ion guide electrodes 984, or only to the third ion guide electrodes and fourth ion guide electrodes (if provided). DC voltages may be applied to some or all of the ion guide electrodes and/or to entrance and exit lenses as needed to control the axial motion of the ions. In some embodiments, DC voltages may be applied to only one pair of opposing electrode sets or to one pair of opposing contiguous conductive layers. In the illustrated embodiment, the first substrate 972 and the second substrate 982 (and thus the first ion guide electrodes 974 and second ion guide electrodes 984) are oriented so as to converge in the direction of the ion guide exit 954, i.e., at an angle to the ion guide axis 950, such that the cross-sectional area of the interior region at the ion guide entrance 952 is greater than the cross-sectional area at the ion guide exit 954. In some embodiments, the ion guide electrodes may be oriented at an angle ranging from about 0.5 degrees to about 10 degrees relative to the ion guide axis 950. The third substrate 986 and the fourth substrate (and thus any ion guide electrodes provided thereon) may likewise converge toward each other relative to the ion guide axis 950, or alternatively may be parallel to each other. In either case, the electrode geometry illustrated in FIG. 9 generates a converging ion confining region 978 as described above.

Similar to the embodiment illustrated in FIG. 8, the ion guide electrodes have relatively small dimensions, resulting in an RF confining field that is maintained in close proximity to the ion guide electrodes and their respective substrates. This configuration may have advantages as noted above. In FIG. 9, the RF confining field is depicted by equipotential lines 994 distributed around each ion guide electrode. Similarly distributed equipotential lines could be visualized around the cross-section of each ion guide electrode in the embodiment of FIG. 8.

In the examples illustrated in FIGS. 8 and 9, the ion acceptance aperture and the ion emittance aperture are each rectilinear in cross-section. In some embodiments, the ion acceptance aperture has a height ranging from about 1 mm to about 3 mm and a width ranging from about 7.5 mm to about 20 mm. In some embodiments, the ion emittance aperture has a height ranging from about 0.05 mm to about 1 mm and a width ranging from about 5 mm to about 15 mm.

In another embodiment (not shown), the ion guide electrodes of the ion guide may generally have a parallel, elongated multipole configuration as schematically shown, for example, in FIG. 1. In this case, a converging ion confining region may be generated by varying the RF confining field such that it has a predominant higher-order multipole field component (e.g., a hexapole component) at the ion guide entrance 152 and a predominant lower-order multipole field component (e.g., a quadrupole component) at the ion guide exit 154. This may be accomplished by applying appropriate RF voltages to the ion guide electrodes 148, which in some embodiments may be axially segmented to facilitate varying the RF confining field for this purpose. A fuller description of this approach and additional examples of electrode arrangements are provided in U.S. Pat. No. 8,124,930, the entire contents of which are incorporated herein by reference.

EXEMPLARY EMBODIMENT

Exemplary embodiments provided in accordance with the presently disclosed subject matter include, but are not limited to, the following:

1. A gas chromatograph-mass spectrometer (GC-MS) system, comprising: a column comprising a column outlet and a plurality of capillaries arranged for establishing respective, simultaneous gas flows to the column outlet; an ionization interface communicating with the column outlet and comprising an ionization device and an ion guide, the ion guide comprising a guide entrance, a guide exit and a plurality of guide electrodes arranged around a guide axis and between the guide entrance and the guide exit, wherein the guide electrodes are configured for constraining ions to an ion beam that radially converges toward the guide exit; and a mass analyzer communicating with the guide exit.

2. The GC-MS system of embodiment 1, wherein the capillaries are open-tubular capillaries or packed capillaries.

3. The GC-MS system of embodiment 1 or 2, wherein each capillary has an inside diameter ranging from 20 μm to 200 μm.

4. The GC-MS system of any of embodiments 1-3, wherein the capillaries have a total inside diameter ranging from 3 mm to 20 mm.

5. The GC-MS system of any of embodiments 1-4, wherein the ionization device is configured for operating at a pressure ranging from 100 Torr to 0.01 Torr.

6. The GC-MS system of any of embodiments 1-5, comprising a vacuum system configured for maintaining the ionization interface at a pressure ranging from 100 Torr to 0.01 Torr.

7. The GC-MS system of any of embodiments 1-6, wherein the ionization device is selected from the group consisting of a photo-ionization device, a chemical ionization device, a field ionization device, a glow discharge device, and a corona discharge device.

8. The GC-MS system of any of embodiments 1-7, wherein the ionization device is positioned upstream of the ion guide, or inside the ion guide.

9. The GC-MS system of any of embodiments 1-8, wherein the ion guide comprises a first ion guide and a second ion guide disposed between the first ion guide and the mass analyzer.

10. The GC-MS system of embodiment 9, comprising a vacuum system configured for maintaining the second ion guide at a lower pressure than the first ion guide.

11. The GC-MS system of any of embodiments 1-10, wherein the guide exit has an inside diameter ranging from 50 to 97% smaller than an inside diameter of the guide entrance.

12. The GC-MS system of any of embodiments 1-11, wherein the guide electrodes are elongated in the direction from the guide entrance to the guide exit and oriented at an angle relative to the guide axis such that one or more opposing pairs of the guide electrodes converge toward the guide exit.

13. The GC-MS system of any of embodiments 1-11, wherein the guide electrodes are elongated in an axial direction from the guide entrance to the guide exit and have respective diameters that vary along the axial direction such that a cross-sectional area of the ion confining region is greater at the guide entrance than at the guide exit.

14. The GC-MS system of any of embodiments 1-11, wherein the guide electrodes are plate-shaped and axially spaced along the guide axis, and the guide electrodes have respective apertures, and wherein the apertures have respective cross-sectional areas that are successively reduced in the direction from the guide entrance to the guide exit.

15. The GC-MS system of any of embodiments 1-11, wherein the plurality of guide electrodes comprises a plurality of first guide electrodes disposed on a first substrate and a plurality of second guide electrodes disposed on a second substrate in radial opposition to the first guide electrodes relative to the guide axis, the first guide electrodes are elongated along the first substrate in the direction from the guide entrance to the guide exit, the second guide electrodes are elongated along the second substrate in the direction from the guide entrance to the guide exit, and the first guide electrodes and the second guide electrodes are oriented at an angle relative to the guide axis such that the first guide electrodes and the second guide electrodes converge toward the guide exit.

16. The GC-MS system of any of embodiments 1-11, wherein the plurality of guide electrodes comprises a plurality of first guide electrodes disposed on a first substrate and a plurality of second guide electrodes disposed on a second substrate in radial opposition to the first guide electrodes relative to the guide axis, the first guide electrodes are spaced from each other along the first substrate in the direction from the guide entrance to the guide exit, the second guide electrodes are spaced from each other along the second substrate in the direction from the guide entrance to the guide exit, and the first substrate and the second substrate are oriented at an angle relative to the guide axis such that a transverse spacing between the first guide electrodes and the second guide electrodes in the radial direction is reduced in the direction from the guide entrance to the guide exit.

17. A method for acquiring a mass spectrum from a sample gas, the method comprising: flowing the sample gas simultaneously through a plurality of capillaries of a gas chromatograph and into an ionization interface; ionizing the sample gas in the ionization interface to produce ions; transmitting the ions through an ion guide and into a mass analyzer; while transmitting the ions, confining the ions to an ion beam that radially converges along an axial length of the ion guide; and while ionizing and transmitting the ions, maintaining the ionization interface at an intermediate pressure between a pressure in the gas chromatograph and a pressure in the mass analyzer.

18. The method of embodiment 17, wherein the sample gas is flowed through the capillaries at a total flow rate ranging from 1 mL/min to 2000 mL/min.

19. The method of embodiment 17 or 18, wherein the intermediate pressure ranges from 100 Torr to 0.01 Torr.

20. The method of any of embodiments 17-19, wherein ionizing comprises operating an ionization device upstream of the ion guide.

21. The method of any of embodiments 17-19, comprising flowing the sample gas into the ion guide, wherein ionizing is performed in the ion guide.

22. The method of any of embodiments 17-21, wherein confining the ions comprises operating the ion guide to apply an RF field to the ions.

23. The method of any of embodiments 17-22, wherein transmitting the ions into the mass analyzer comprises operating the ion guide to accelerate the ions.

24. The method of any of embodiments 17-23, comprising, while confining the ions, reducing the kinetic energy of the ions.

25. The method of embodiment 24, wherein reducing comprises flowing a damping gas into the ionization interface.

26. The method of any of embodiments 17-25, wherein the ion guide comprises a first ion guide and a second ion guide, and transmitting the ions comprises transmitting the ions as a converged beam through the first ion guide at a first intermediate pressure, and transmitting the ions as a converged beam through the second ion guide at a second intermediate pressure lower than the first intermediate pressure.

27. The method of embodiment 26, wherein the first intermediate pressure ranges from 100 to 5 Torr, and the second intermediate pressure ranges from 5 to 0.01 Torr.

28. A gas chromatograph-mass spectrometer system configured for performing the method of any of embodiments 17-27.

It will be understood that the term "in signal communication" as used herein means that two or more systems, devices, components, modules, or sub-modules are capable of communicating with each other via signals that travel over some type of signal path. The signals may be communication, power, data, or energy signals, which may communicate information, power, or energy from a first system, device, component, module, or sub-module to a second system, device, component, module, or sub-module along a signal path between the first and second system, device, component, module, or sub-module. The signal paths may include physical, electrical, magnetic, electromagnetic, electrochemical, optical, wired, or wireless connections. The signal paths may also include additional systems, devices, components, modules, or sub-modules between the first and second system, device, component, module, or sub-module.

More generally, terms such as "communicate" and "in . . . communication with" (for example, a first component "communicates with" or "is in communication with" a second component) are used herein to indicate a structural, functional, mechanical, electrical, signal, optical, magnetic, electromagnetic, ionic or fluidic relationship between two or more components or elements. As such, the fact that one component is said to communicate with a second component is not intended to exclude the possibility that additional components may be present between, and/or operatively associated or engaged with, the first and second components.

It will be understood that various aspects or details of the invention may be changed without departing from the scope of the invention. Furthermore, the foregoing description is for the purpose of illustration only, and not for the purpose of limitation—the invention being defined by the claims.

What is claimed is:

1. A gas chromatograph-mass spectrometer (GC-MS) system, comprising:
 a column comprising a column outlet and a plurality of capillaries arranged for establishing respective, simultaneous gas flows to the column outlet;
 an ionization interface communicating with the column outlet and comprising an ionization device and an ion guide, the ion guide comprising a guide entrance, a guide exit and a plurality of guide electrodes arranged around a guide axis and between the guide entrance and the guide exit, wherein the guide electrodes are configured for constraining ions to an ion beam that radially converges toward the guide exit; and
 a mass analyzer communicating with the guide exit.

2. The GC-MS system of claim 1, wherein each capillary has an inside diameter ranging from 20 μm to 200 μm.

3. The GC-MS system of claim 1, wherein the ionization device is configured for operating at a pressure ranging from 100 Torr to 0.01 Torr.

4. The GC-MS system of claim 1, comprising a vacuum system configured for maintaining the ionization interface at a pressure ranging from 100 Torr to 0.01 Torr.

5. The GC-MS system of claim 1, wherein the ionization device is selected from the group consisting of a photo-ionization device, a chemical ionization device, a field ionization device, a glow discharge device, and a corona discharge device.

6. The GC-MS system of claim 1, wherein the ionization device is positioned upstream of the ion guide, or inside the ion guide.

7. The GC-MS system of claim 1, wherein the ion guide comprises a first ion guide and a second ion guide disposed between the first ion guide and the mass analyzer.

8. The GC-MS system of claim 7, comprising a vacuum system configured for maintaining the second ion guide at a lower pressure than the first ion guide.

9. The GC-MS system of claim 1, wherein the guide exit has an inside diameter ranging from 50 to 97% smaller than an inside diameter of the guide entrance.

10. A method for acquiring a mass spectrum from a sample gas, the method comprising:
 flowing the sample gas simultaneously through a plurality of capillaries of a gas chromatograph and into an ionization interface;
 ionizing the sample gas in the ionization interface to produce ions;
 transmitting the ions through an ion guide and into a mass analyzer;
 while transmitting the ions, confining the ions to an ion beam that radially converges along an axial length of the ion guide; and
 while ionizing and transmitting the ions, maintaining the ionization interface at an intermediate pressure between a pressure in the gas chromatograph and a pressure in the mass analyzer.

11. The method of claim 10, wherein the sample gas is flowed through the capillaries at a total flow rate ranging from 1 mL/min to 2000 mL/min.

12. The method of claim 10, wherein the intermediate pressure ranges from 100 Torr to 0.01 Torr.

13. The method of claim 10, wherein ionizing comprises operating an ionization device upstream of the ion guide.

14. The method of claim 10, comprising flowing the sample gas into the ion guide, wherein ionizing is performed in the ion guide.

15. The method of claim 10, wherein transmitting the ions into the mass analyzer comprises operating the ion guide to accelerate the ions.

16. The method of claim 10, comprising, while confining the ions, reducing the kinetic energy of the ions.

17. The method of claim 16, wherein reducing comprises flowing a damping gas into the ionization interface.

18. The method of claim 10, wherein the ion guide comprises a first ion guide and a second ion guide, and transmitting the ions comprises transmitting the ions as a converged beam through the first ion guide at a first intermediate pressure, and transmitting the ions as a converged beam through the second ion guide at a second intermediate pressure lower than the first intermediate pressure.

19. The method of claim 18, wherein the first intermediate pressure ranges from 100 to 5 Torr, and the second intermediate pressure ranges from 5 to 0.01 Torr.

20. A gas chromatograph-mass spectrometer system configured for performing the method of claim 10.

* * * * *